United States Patent [19]

Sun et al.

[11] Patent Number: 5,238,652

[45] Date of Patent: Aug. 24, 1993

[54] ANALYTICAL TEST DEVICES FOR COMPETITION ASSAY FOR DRUGS OF NON-PROTEIN ANTIGENS USING IMMUNOCHROMATOGRAPHIC TECHNIQUES

[75] Inventors: Ming Sun, Cherry Hill; Francis R. Pfeiffer, Cinnaminson, both of N.J.

[73] Assignee: Drug Screening Systems, Inc., Blackwood, N.J.

[21] Appl. No.: 540,844

[22] Filed: Jun. 20, 1990

[51] Int. Cl.$^5$ .................. G01N 33/546; G01N 33/483
[52] U.S. Cl. ........................... 422/61; 422/58; 436/523; 436/531; 436/533; 436/63; 436/164; 436/901; 435/810
[58] Field of Search ........................ 422/56–58, 422/61; 436/523, 528, 533, 63, 531, 164, 901; 435/7.1, 810

[56] References Cited

U.S. PATENT DOCUMENTS

| | | |
|---|---|---|
| 4,594,327 | 6/1986 | Zuk . |
| 4,740,468 | 4/1988 | Weng et al. . |
| 4,745,075 | 5/1988 | Hadfield et al. . |
| 4,774,174 | 9/1988 | Giegel et al. . |
| 4,803,170 | 2/1989 | Stanton et al. ............ 436/518 |
| 4,829,010 | 5/1989 | Chang . |
| 4,857,453 | 8/1989 | Ullman et al. . |
| 4,868,132 | 9/1989 | Byrnes et al. . |
| 4,938,927 | 7/1990 | Kelton ............ 422/64 |
| 4,943,522 | 7/1990 | Eisinger et al. . |
| 4,952,520 | 8/1990 | Okusa et al. ............ 436/534 |
| 4,956,275 | 9/1990 | Zuk et al. . |
| 5,026,653 | 6/1991 | Lee et al. ............ 422/58 |
| 5,141,875 | 8/1992 | Kelton ............ 436/514 |

*Primary Examiner*—James C. Housel
*Assistant Examiner*—Lyle A. Alexander
*Attorney, Agent, or Firm*—Eckert Seamans Cherin & Mellott

[57] ABSTRACT

An analytical test device for competition assay for particular non-protein antigens, such as antigens representing drugs of abuse, is disclosed. The analytical test device is a test kit housing having an opening for introduction of a body fluid sample and a flow path for the body fluid sample. A supply of microscopic colored latex particles is adjacent to the opening along the flow path. A chromatographic membrane support is within the test kit housing for exposing the colored latex particles to the body fluid sample. When non-protein antigens are not present in the body fluid specimen, the colored latex particles accumulate at a predetermined site on the chromatographic membrane by complexing of antibodies on the colored latex particles to a drug conjugate probe on the membrane support to leave a visually perceptible colored mark of the same color as the colored latex particles. When non-protein antigens are present in the body fluid specimen, complexing of the non-protein antigens to the supply of antibodies on the colored latex particles exhausts the antibody supply on the colored latex particles such that the colored latex particles cannot complex to the immobilized drug conjugate probe, leaving no visually perceptible colored mark at the predetermined site. Also disclosed is a process for analytical testing of a body fluid for the presence of non-protein antigens, and an analytical test assembly for simultaneous multiple competition assays.

24 Claims, 11 Drawing Sheets

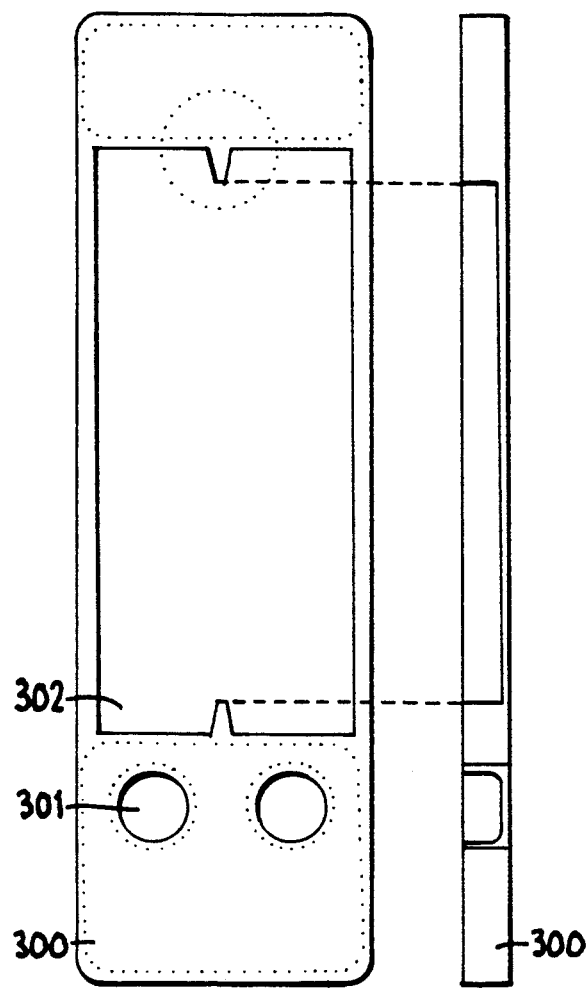

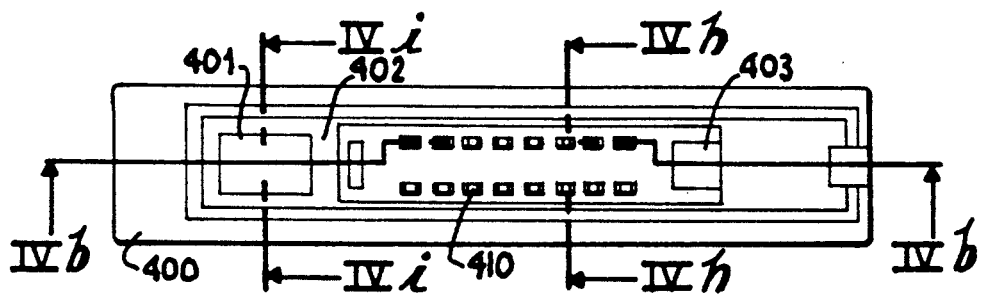
Fig. 4a.
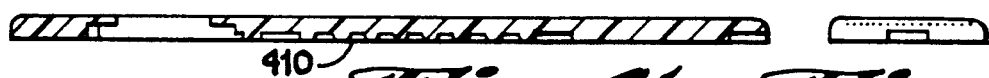
Fig. 4b.  Fig. 4g.
 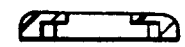
Fig. 4h.  Fig. 4i.
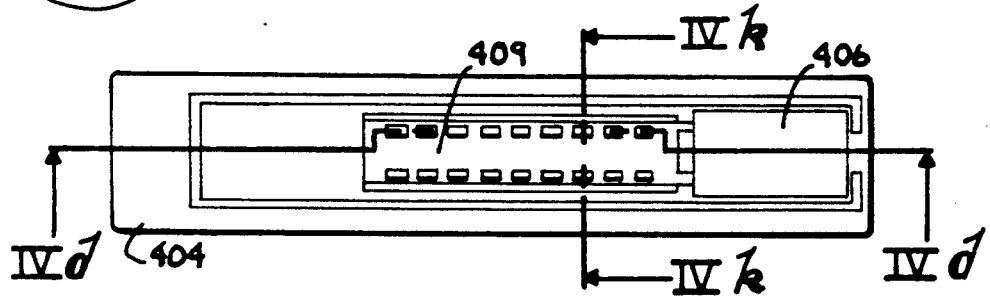
Fig. 4c.
 
Fig. 4d.  Fig. 4j.
Fig. 4k.

ANALYTICAL TEST DEVICES FOR COMPETITION ASSAY FOR DRUGS OF NON-PROTEIN ANTIGENS USING IMMUNOCHROMATOGRAPHIC TECHNIQUES

BACKGROUND OF THE INVENTION

1. Field of the Invention

The invention relates to analytical test devices which use immunochromatographic assays formulated on a competitive immunochemical protocol, and which determine small hapten, non-protein molecules such as those representing the presence of drugs of abuse. More particularly, the invention relates to self-contained analytical devices which require only the addition of a few drops of body fluid such as urine or other liquid to initiate a complex, multi-step immunoassay that produces a visually perceptible precipitin via antigen/antibody reactions, and which do not require instrumentation or sophisticated training to assess the results. The invention further relates to housing articles useful for packaging kits for these immunoassays, to novel reagents, and to methods for utilizing the novel reagents in the test devices which simultaneously can assay in a single device for up to five (5) of the National Institute of Drug Abuse (NIDA) designated drugs of abuse recommended in a drug screen.

2. Prior Art

The measurement of physiologically important substances in urine, serum and tissue with immunological principles is an important recent development in immunology (V. P. Butler, *Pharmocol. Reviews* (1978), 29, 103-184). In particular, drug-specific antibodies and antigens have been used in the development of a variety of immunological assay procedures for the detection and/or quantification of antibodies or antigens in the bodily fluids of humans and animals. Immunoassay methods have distinct advantages when compared, for example, with techniques using thin layer chromatography, gas chromatography, gas chromatography/mass spectroscopy or high performance liquid chromatography because of the high specific accuracy associated with immunoassays and their ease of use.

Most immunological testing procedures are focused upon the antigen-antibody reaction or competition which provides an end point with an insoluble or agglutinated precipitate (E. A. Kabat, *Methods in Enzymology*, Vol. 70 (1980), Academic Press, New York, pp. 3-49). Existing non-isotopic immunoassay test kits are based on enzyme-linked immunosorbent assay (ELISA), homogeneous enzyme multipled immunoassay techniques (EMIT), latex agglutination assays and fluorescent polarization immunoassay. More recently, membrane-based particle immunoassays have been reported for human pregnancy tests which measure the level of human chorionic gonadotropin (HCG) (UK Patent Application, GB 2,204,398A, Apr. 26, 1988). These assay procedures generally have the disadvantage of requiring multi-step protocols, multiple reagents, reagent storage problems, and the need of special designed instrumentation or specially trained personnel to assess and record the test results. Specific immunoassays using reagent-impregnated test strips and latex particles have been reported in U.S. Pat. Nos. 3,857,931; 4,094,647; 4,690,907; and 4,740,468; G.B. Patent 1,589,234; European patents 0,225,054; 0,138,442; and 0,136,799; and in G.B. Patent Application 2,204,398A (Unilever).

There is a need for a test and/or device which is simple to use and which can be used anywhere rather than only in a laboratory setting, which via competition of the analyte, or drug, and the analyte conjugate for limited antibody binding sites, can identify presence or absence of drugs of abuse in humans, and which does not require instrumentation to read the end results. The test devices of this invention will detect drugs of abuse, for example, in a stable immunoassay configuration using certain novel protein conjugates of these drugs of abuse, and the accompanying antibodies. There is also a need for a self-contained analytical testing device which can simultaneously perform assays for multiple drugs of abuse in a single device.

SUMMARY OF THE INVENTION

It is an object of the invention to provide a test device to identify the presence of small hapten, non-protein antigens such as drugs of abuse.

It is another object of the invention to provide a self-contained analytical test device which requires only the addition of a few drops of test liquid to initiate an immunoassay which proceeds through a plurality of steps by inherent characteristics of the test device.

It is a further object of the invention to provide an analytical test device which does not require instrumentation or sophisticated personnel to obtain and read the results.

It is still another object of the invention to provide an easily ascertainable visual identification of the drugs and/or metabolites of drugs of abuse in urine processed using a simple test kit.

It is still another object of the invention to provide an analytical test device which can simultaneously perform assays for multiple drugs of abuse.

These and other objects are accomplished by a test device which uses various immunochemical based configurations embodied in an immunochromatographic system. The test devices use small antigen conjugates, have precipitin end points with hapten detection capabilities, contain chromatographic supports made of impregnated membranes, and offer accuracy as well as ease of use in non-laboratory settings. The test devices require only the addition of a few drops of urine, biological fluids or aqueous solutions. At least five drugs of abuse can be tested simultaneously in a single device. The five drugs of abuse recommended by the NIDA for a drug screen, namely amphetamines/methamphetamines, cocaine, opiates, phencyclidine, and cannabinoids, are thus readily detectable simultaneously using a simple test kit.

BRIEF DESCRIPTION OF THE DRAWINGS

There are shown in the drawings the embodiments of the invention that are presently preferred. It should be understood, however, that the invention is not limited to the precise arrangements and instrumentalities shown in the drawings, wherein:

FIG. 1b is a side view of the test device of FIG. 1a.

FIG. 2b a side section view of the top piece of FIG. 2a.

FIG. 3a is a top view of a test device holder for use in a test device assembly according to the invention.

FIG. 3b is a side sectional view of the test device holder of FIG. 3a.

FIG. 3c is an end sectional view of the test device holder of FIG. 3a.

FIG. 3g is a top view of a test device assembly according to the invention.

FIG. 4a is a top view of a top piece of an alternative embodiment of a test device according to the invention.

FIG. 4b is a side sectional view of the top piece of FIG. 4a.

FIG. 4c is a top view of a bottom piece of an alternative embodiment of a test device according to the invention.

FIG. 4d is a side sectional view of the bottom piece of FIG. 4c.

FIG. 4g is an end view of the top piece of FIG. 4a.

FIG. 4h is an end sectional view of the top piece of FIG. 4a taken along line 4h—4h.

FIG. 4i is an end sectional view of the top piece of FIG. 4a taken along line 4i—4i.

FIG. 4j is an end view of the bottom piece of FIG. 4c.

FIG. 4k is an end sectional view of the bottom piece of FIG. 4c taken along line 4k—4k.

DETAILED DESCRIPTION OF THE PREFERRED EMBODIMENTS

Figure 1A:
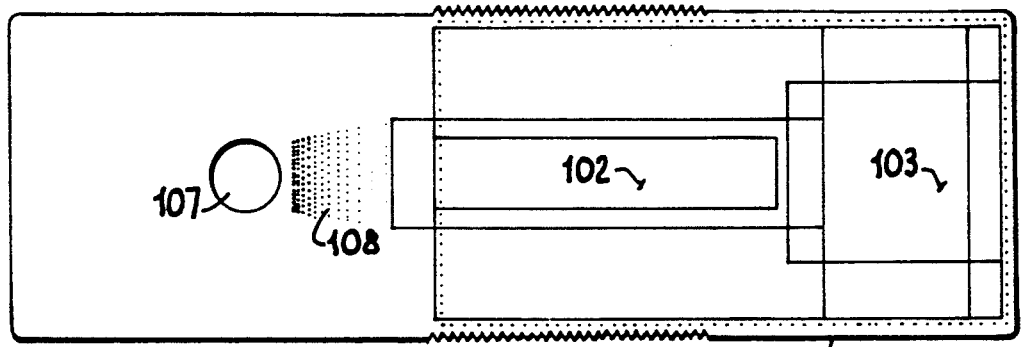
FIG. 1a is a top view of a test device according to the invention.

The present invention improves and adopts certain known immunological techniques involving laboratory procedures (A. J. Weiss and L. A. Blankstein, Amer. Clin. Prod. Review (1987), 6, 8–19), including those reported in the above publications, to obtain analytical test devices applicable for the assay of non-protein antigens such as drugs of abuse. The test devices are quick and convenient to use by non-sophisticated personnel in non-laboratory settings, and perform assays for up to five drugs of abuse simultaneously. The multiple competition assays are housed in a single device and result in easily discernable visual end points that do not require instrumentation to interpret.

The test devices contain all of the components for a specific immunoreaction, and provide an appropriate visual end point which detects or identifies the presence or absence of drugs of abuse in the test sample.

The test devices of the invention comprise:

a test kit housing having means for introduction of a body fluid sample and means defining a flow path for the body fluid sample;

a supply of microscopic colored latex particles disposed adjacent to the means for introduction of the body fluid sample along the flow path, the colored latex particles becoming suspended in the body fluid sample and moving with flow of the body fluid sample along the flow path, the latex particles being sensitized with a supply of antibodies for the non-protein antigen at least on a surface thereof, said antibodies being responsive to said non-protein antigens and being operable to complex therewith;

a chromatographic membrane support disposed within the test kit housing and being impregnated at a predetermined site along the flowpath downstream of the colored latex particles with an immobilized drug conjugate probe sensitive to said antibodies of the latex particles, and operable to complex therewith; and, means for exposing the colored latex particles to the body fluid sample for substantially complete reaction of the non-protein antigens in the body fluid sample with the antibodies for the non-protein antigen on the latex particles, prior to the body fluid sample reaching the predetermined site along the flow path;

whereby when said non-protein antigens are not present in the body fluid sample the latex particles accumulate at the predetermined site by complexing of the antibodies on the latex particles with the drug conjugate probe on the membrane support to leave a visually perceptible colored mark, and when the non-protein antigens are present in the body fluid sample, complexing of the non-protein antigens to the supply of antibodies on the latex particles substantially exhausts the antibody supply on the latex particles such that the latex particles cannot complex to the immobilized drug conjugate probe, leaving no visually perceptible mark at the predetermined site.

The elongated moisture impervious housing provides an opening for the introduction of body fluid samples to the test device. The opening in the moisture impervious housing permits the introduction of small quantities of human body fluids into the housing. An absorbent well containing an absorbent pad is in communicating relationship with the housing opening.

The porous chromatographic membrane support located within the housing may be a nitrocellouse membrane such as that available from Schleicher & Schuell, Inc. or a nylon membrane such as that available from Amicon under the AUTOBLOC trademark. Such porous membranes have the natural ability to bind proteins, and immunoreagents can be applied directly to the membranes and immobilized thereon. The membranes are available in a broad range of pore sizes which provides a range of carrier materials which can be selected for test devices for particular drugs of abuse. Generally, the membranes have from about 1.0 to about 12.0 micron pore sizes, preferably from about 5 to 12 micron pore sizes.

The porous chromatographic membrane support is impregnated with a specific antigen or probe such as a drug conjugate probe. For example, antigens of derivatives thereof for any of the five drugs of abuse recognized by the NIDA may be impregnated on the membrane. A benzoylecgonine derivative is the antigen which is impregnated to identify the presence or absence of cocaine in the tested body fluid sample. A carboxy methylmorphine derivative conjugate with bovine serum albumin is the antigen to detect the presence or absence of opiates such as morphine. A methamphetamine conjugate is used as the antigen to test for the presence or absence of amphetamines and methamphetamines, and a phencyclidine conjugate or a tetrahydrocannabinoid conjugate are respectively impregnated to determine the presence or absence of phencyclidine or cannabinoids in body fluids.

The volume of drug conjugate probe immobilized on the membrane ranges from about 0.1 to about 10 microliters per centimeter.

A second immobilized immuno reaction probe is applied to the membrane downstream of the drug conjugate probe. The second immuno reaction probe is a protein antigen and the second probe serves as a test or indicator that the analytical test device is operative. Any available protein antigen can be selected for the second immuno reaction probe. The protein is applied or impregnated on the membrane at a concentration of from about 0.1 to about 10 milligrams per milliliter.

The third component impregnated on the chromatographic membrane support is an area of colored microscopic latex spheres. The latex spheres are sensitized or coated with detecting antibodies for the non-protein antigen or drug of abuse or their metabolites, and an antibody for the second or protein probe. The latex spheres may be from about 0.1 to about 1 micron in diameter. The latex spheres may be colored in any desirable color such as red, blue or green, blue being the preferred color. The latex spheres are applied to the membrane in an area from about 1 to about 10 millimeters in width. The latex spheres are applied to the membrane upstream of the immobilized drug conjugate probe, and in close proximity to the opening of the housing and the absorbent pad found therein. The latex spheres are immobile when applied to the membrane although, in contrast with the drug conjugate probe and the immuno reaction probe, the latex spheres become mobile when in contact with moisture.

The latex spheres are coated with a detecting antibody for the non-protein antigen. The detecting antibody will vary depending upon the drug of abuse which is detected in the housing. The latex spheres will also be coated with an antibody for the immuno reactive antigen and probe downstream of the drug conjugate probe. The latex spheres preferably are bathed with a protein agent to coat the entire circumference of the sphere to facilitate movement of the spheres as they traverse the chromatographic membrane.

To use the analytical test device to detect the presence of or absence of non-protein antigens such as drugs of abuse in body fluids, a body fluid sample, such as a sample of urine is introduced to the opening within the moisture impervious housing. The body fluid sample is absorbed on the pad beneath the opening and capillary action results in contact between the body fluid sample and the colored latex spheres. The urine or body fluid combines with the spheres after a short time of incubation, perhaps three to five minutes, for example. In the event that the body fluid sample being tested contains a drug of abuse or its metabolite, it will immediately bind with or complex with the antibody present on the latex sphere. Should this occur, there will be no free detecting antibody present on the latex spheres as they migrate or traverse the membrane and reach the immobilized drug conjugate probe. This will prevent the attachment of the colored latex spheres to the site of the drug conjugate probe on the membrane, a fact which will be indicated by the absence of a colored line in the area of the drug conjugate probe. Therefore, a positive test urine sample will be demonstrated or indicated by the absence of the colored line or indication at the area of the drug conjugate probe.

The latex spheres will continue their migration and traversal of the membrane where the protein antibody on the latex spheres will complex with the protein antigen immobilized on the second probe. The result of this complex will be the appearance of a colored line on the probe, a fact which demonstrates the viability of the test device. This means that a negative test urine sample will produce two colored lines on the membrane, whereas, as stated above, a positive test urine sample will produce only one line.

No special reagents or conditions are required for completion of the analytical test. Moreover, there is no need for sophisticated personnel to complete the test.

Figure 1B:
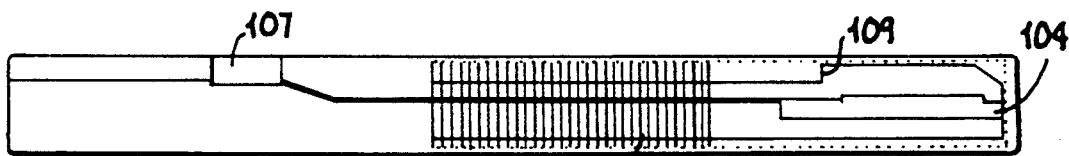

The invention comprises several designs for the devices and analytical procedures. FIGS. 1a and 1b show an analytical test device 100 which has two pieces of plastic that are welded to fabricate a plastic housing of a test device. The plastic used for these devices may be clear or opaque, for example of a polymer or copolymer material as known to those skilled in the art of mold or cavity casting. Within this device is a porous chromatographic membrane 102 which is impregnated with immunochemical agents and has an absorbent pad placed at slot 103. A reception cavity 107 communicates with the membrane through a passage channel 108. An aperture for an air equalization outlet is located at 104. When an outside sleeve 105 is displaced by gripping along a serrated side 106, a view window area is revealed, and this action can be arranged to create an air displacement or vacuum by expanding a compartment downstream from a sample well, which thereby draws or pulls the aqueous mixture containing the analyte away from the reception cavity and into a path leading toward the predetermined site of the antigen at which a visual mark may be produced. This action initiates movement of the liquid through the passage channel 108 and onto the porous membrane 102. The passage channel 108 preferably has a coarse surface to effectively prevent the free flow of the sample and reagent mixture toward the self-contained membrane until such vacuum pulling action is initiated to commence flow.

When the aqueous mixture is drawn into the passage channel 108, the passage channel assists in at least one of mixing and incubation of the analyte solution and immunochemical components of the test kit, contained in the well 107 or in the channel, in the kit as provided. This device allows for the deposition of the reagents onto the membrane. The reagents may include for example, antibody-coated colored particles, which can be freeze dried in a carrier buffer comprising protein stabilizers.

Sample urine solutions, for example, are added dropwise to the reception cavity 107 to suspend the particles and solubilize the other reagents in the well. After sufficient time for mixing and incubation (3 to 5 minutes, for example), the aqueous mixture is allowed to enter the passage channel and come in contact, via capillary action, with the carrier membrane after the movement of the sleeve 105 is completed. The stop catch 109 allows for the sleeve to move the appropriate length, whereupon the sleeve is stopped. The colored particles pass with flow assisted by capillary action along the membrane. When the colored particles complex, they are immobilized on the membrane through specific antibody/antigen reactions with antibodies or antigens provided on the membrane at predetermined location. This produces a precipitin color end point defining for example a line, specific design or symbol which is visible at said location.

In the competition assay technique, when the test sample is positive for a particular analyte or hapten, such as, for example, a drug of abuse or a metabolite of a drug of abuse, the antibody which might be absorbed on a latex particle on the membrane, for example, this specific test analyte or hapten, is blocked due to previous absorption of the analyte in the test sample. This prevents the formation of a precipitin end point.

A reference immuno reaction probe or communicant can be added to the chromatographic support, flowing to a point downstream of the predetermined location. The appearance of a color end point then informs the user of the completion of an analytical test run as well as indicating the stability or viability of the test components. This reference probe or communicant line can be constructed, for example, with a second antibody/antigen reaction or with other configurations such as, for example, an avidin/biotin interaction.

Figure 2A:
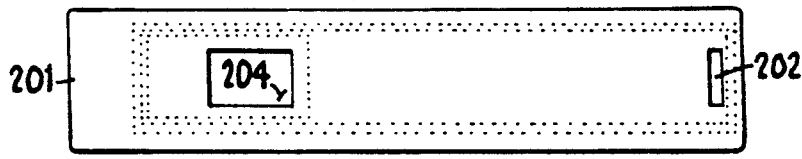
FIG. 2a is a top view of a top piece of a test device according to the invention.
Figure 2I:
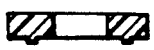
FIG. 2i is an end section view of the top piece of FIG. 2b.
Figure 2B:
Figure 2J:
FIG. 2j is an end section view of a reception cavity of the top piece of FIG. 2b.
Figure 2C:
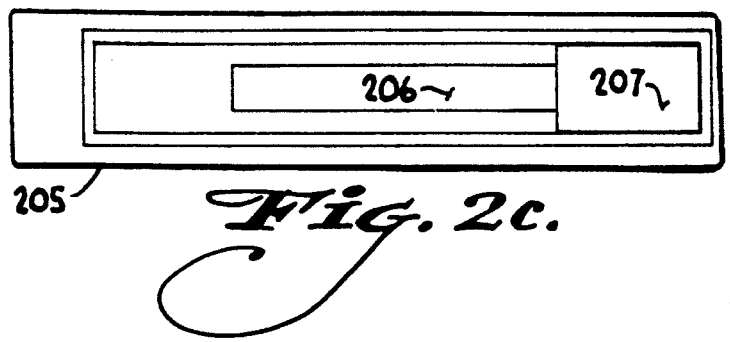
FIG. 2c is a top view of a bottom piece of a test device according to the invention.
Figure 2D:
FIG. 2d is a side section view of the bottom piece of FIG. 2c.
Figure 2K:
FIG. 2k is an end view of the bottom piece of FIG. 2d.
Figure 2E:
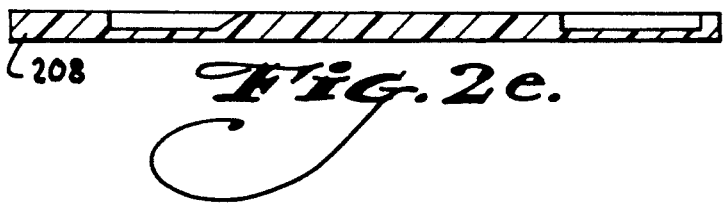
FIG. 2e is a side section view of an alternative embodiment of a bottom piece having a dish-like sample well.
Figure 2L:
FIG. 2l is an end section view of the bottom piece of FIG. 2e.
Figure 2F:
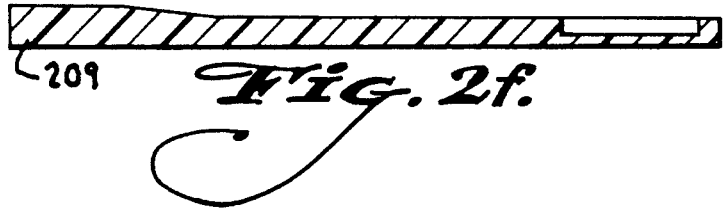
FIG. 2f is a side section view of an alternative embodiment of a bottom piece having an inclined sample well.
Figure 2M:
FIG. 2m is an end section view of the bottom piece of FIG. 2f.
Figure 2G:
FIG. 2g is a top view of a test device having the top piece of FIG. 2a and the bottom piece of FIG. 2c.
Figure 2H:
FIG. 2h is a side section view of the test device of FIG. 2g.

FIGS. 2a–2m illustrate another embodiment of a test device according to the invention. A top piece of the housing 201, reception cavity 203, reception cavity opening 204, air outlet 202, bottom half of the device 205, frame for receiving the chromatographic support membrane, and absorbent pad location 207 are included. Test sample liquid is delivered into the reception cavity opening 204 of the device 200. The sample well may or may not have an absorbent pad therein. Additionally or alternatively the device can define dish-like sample well 208, as shown in FIG. 2e, which facilitates sample capillary migration. As shown in FIG. 2f, the sample well is inclined such that it slopes into the membrane chamber. When the device 200 is fully assembled, the top and bottom pieces are welded along a junction line, and a removable tape covers the air outlet 202. This configuration produces a partially closed system that prevents premature migration of the aqueous solution of the sample and the mobile colored particles, down the membrane to the predetermined site of the fixed antigens/antibodies before proper mixing, incubation and equilibration of the liquid carried components of the test is achieved. After a sample or sample reagent are introduced into the device, sufficient time and/or mixing is permitted to ensure that tests are accurate. The migration can then be initiated by lifting the tape at the air outlet to create a solvent flow down the membrane. As the liquid sample migrates through the porous support, the colored particles form an indicator visual end point from the specific antigen/antibody reaction. The presence of free analyte in the sample solution competes with the immobilized binding sites of the antibody or antigen specific for the analyte, and the formation of precipitin end point is inhibited.

Figures 3D, 3E:
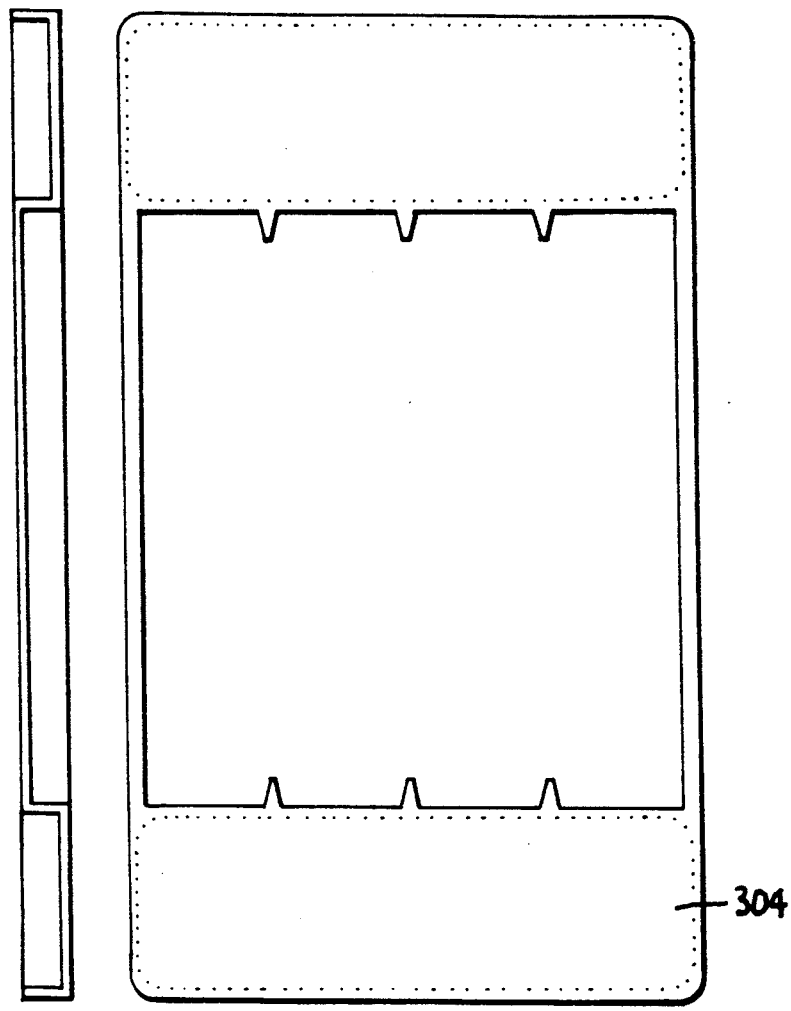
FIG. 3d is a top view of an alternative embodiment of a test device holder for use in a test device assembly according to the invention.
FIG. 3e is a side sectional view of the test device holder of FIG. 3d.
Figure 3F:
FIG. 3f is an end sectional view of the test device holder of FIG. 3d.
Figure 3H:
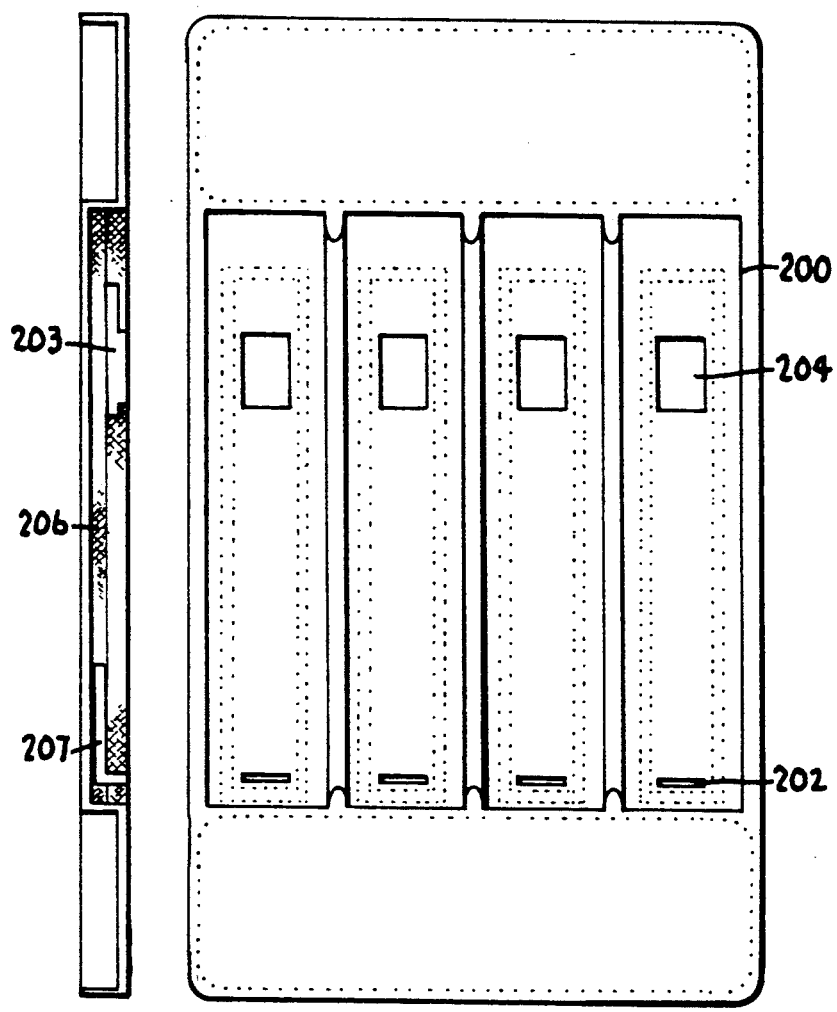
FIG. 3h is a side sectional view of the test device assembly of FIG. 3g.
Figure 3I:
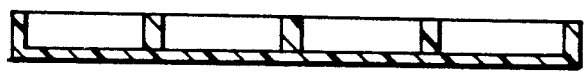
FIG. 3i is an end sectional view of the test device assembly of FIG. 3g.
Figure 4E:
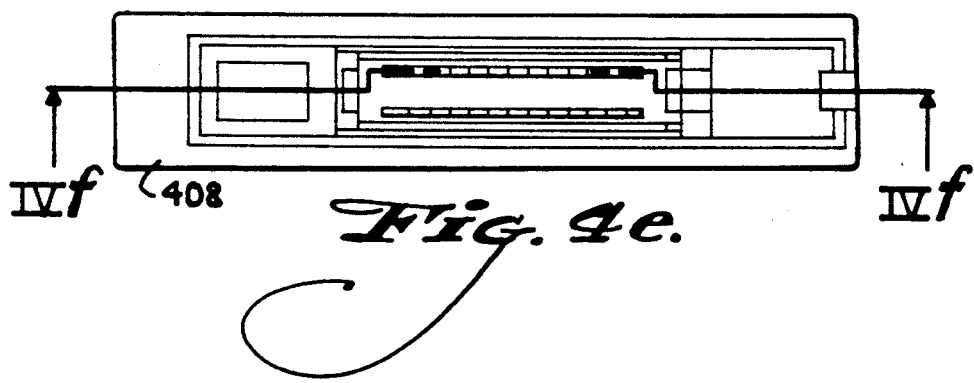
FIG. 4e is a top view of a test device having the top piece of FIG. 4a and the bottom piece of FIG. 4c.
Figure 4F:
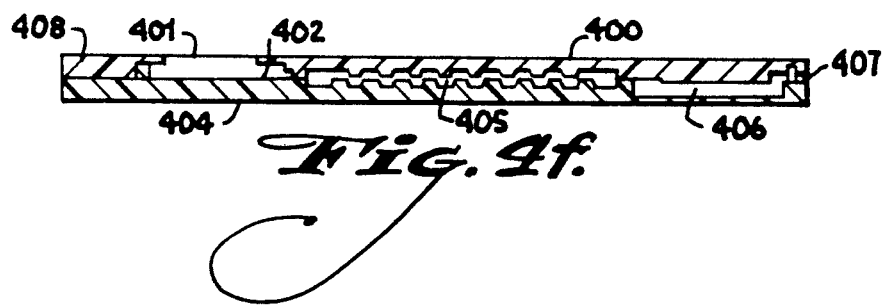
FIG. 4f is a side sectional view of the test device of FIG. 4e.

FIG. 3a depicts the holder design 300 for use with two plastic housings, such as, for example, devices 100, 200, 408, 500 and 608. The two external wells 301 are located in the holder 300 adjacent to each test device. The two slots 302 hold two plastic housing test devices. The external well 301 is used to deposit particles on which antibody or antigen are absorbed. When a liquid test sample is added to the well charged with the particles, the previously freeze dried particle mass is then suspended in the aqueous test sample. After a period of incubation, for example, 3 to 5 minutes, the test mixture is then transferred to the corresponding test device. Another version of the holder is illustrated in FIG. 3d. The holder 304 has four slots in which four different test device units are contained, such as, for example, devices 100, 200, 408, 500 and 608. FIG. 3g shows a complete test device assembly having four test devices fitted in a holder.

FIGS. 4a–4k show device 408 which is another version of a test device. The chromatographic membrane 409 is essentially suspended in a chamber 405 between bottom piece 404 and top piece 400. Teeth 410 extended from the top and bottom pieces and hold the membrane between their opposing ends. When a liquid sample is deposited in the opening 401, the aqueous solution percolates through the absorbing or filter pad 402 onto and down the membrane pretreated with probes or communicant materials. An absorbing pad 406 is in contact with the membrane or porous material to receive the test sample fluid after the liquid has traveled through the membrane.

Figure 5:
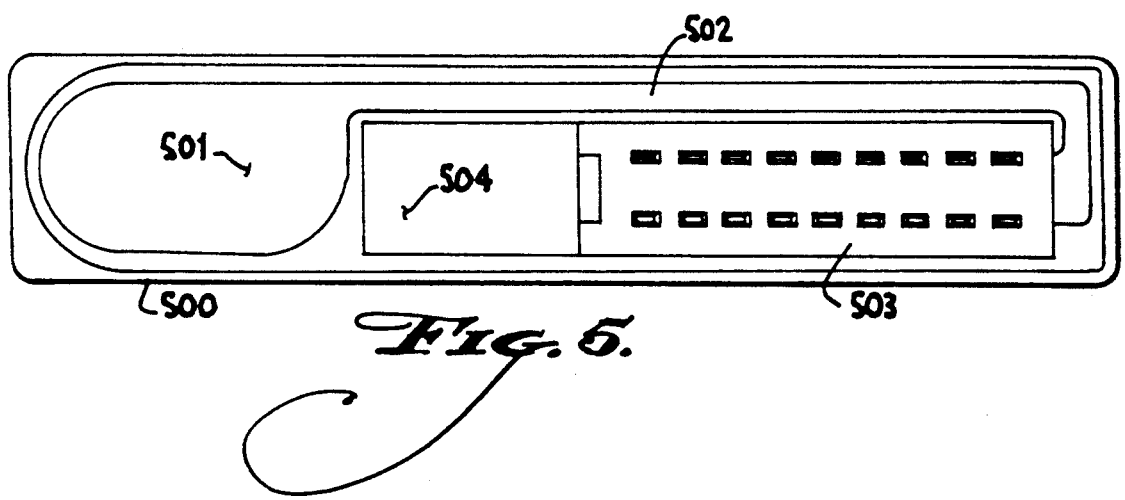
FIG. 5 is a top view of an alternative embodiment a test device having a capillary passage.
Figure 6A:
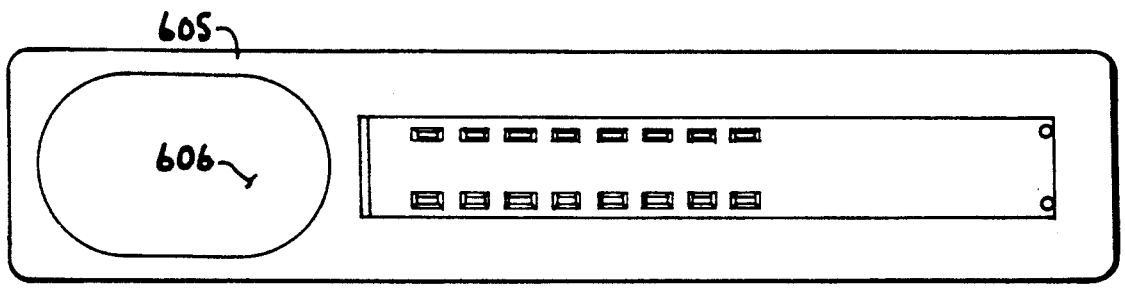
FIG. 6a is a top view of a top piece of an alternative embodiment of a test device according to the invention.
Figure 6B:
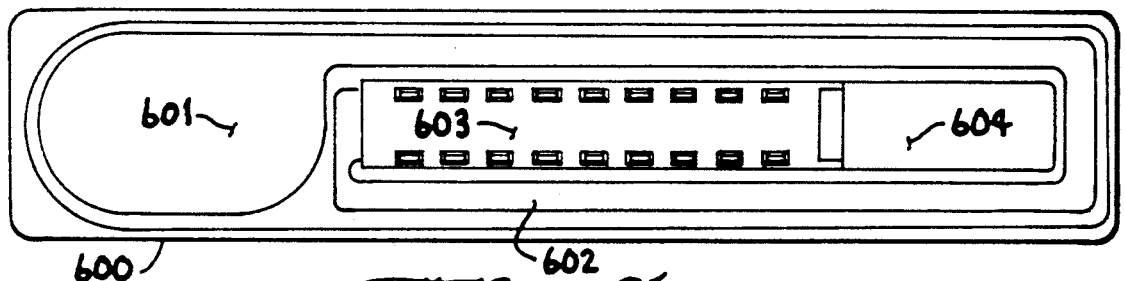
FIG. 6b is a top view of a bottom piece of an alternative embodiment of a test device according to the invention.
Figure 6C:
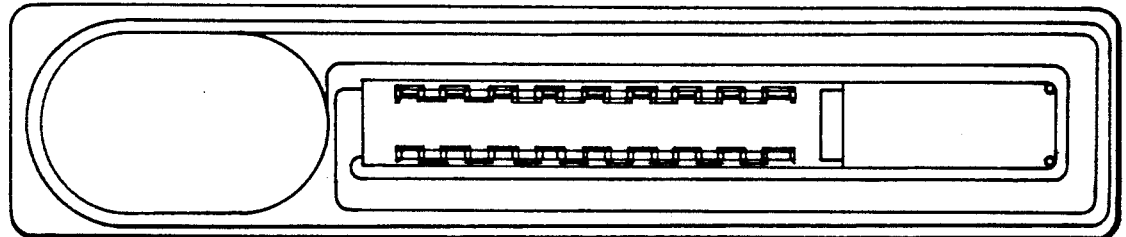
FIG. 6c is a top view of a test device having the top piece of FIG. 6a and the bottom piece of FIG. 6b.

FIG. 5 represents a different configuration of a test device 500 in which an aqueous sample is first allowed to mix with the latex particles in the sample well 501 to facilitate equilibration, incubation and mixing of the imaunochemicals with the sample. The mixture is then introduced or channeled into the capillary passage 502 for movement via capillary action toward a membrane located at 503. During the migration of the test sample mixture down the capillary passage, the analytes in the sample or the particles containing antigen and/or antibody have time to mix, react and complex as a prelude to migrating through the porous material that contains the probes or communicants which give the precipitin end point as described for device 100. The absorbent pad is found at 504. The test device represented in FIGS. 6a-6c is a further extension of the device described in FIG. 5 except that the capillary passage 602 is extended to go completely around the membrane housed at 603 to allow for additional incubation of the reactants. The test device 608 contains an absorbing pad 604 at the end of the chromatographic path. The top piece of the device 605, sample well opening 606, bottom piece 600 and reception cavity 601 are as marked.

A further extension of the test devices and configurations allows more than one assay to be accomplished in a single housing unit such as 100, 200, 408, 500 and 608. In this configuration, two or more analytes can be assayed on the same membrane by the addition of the antibodies/antigens specific for each test such that appropriate probe or communicant end points can be ascertained which are distinct for each analyte. This membrane has antigen conjugate probe lines corresponding to the specific antibodies/antigens that are absorbed on the latex particles. The housings, holders, test protocols and end points are as described previously for the assays.

Figure 7A:
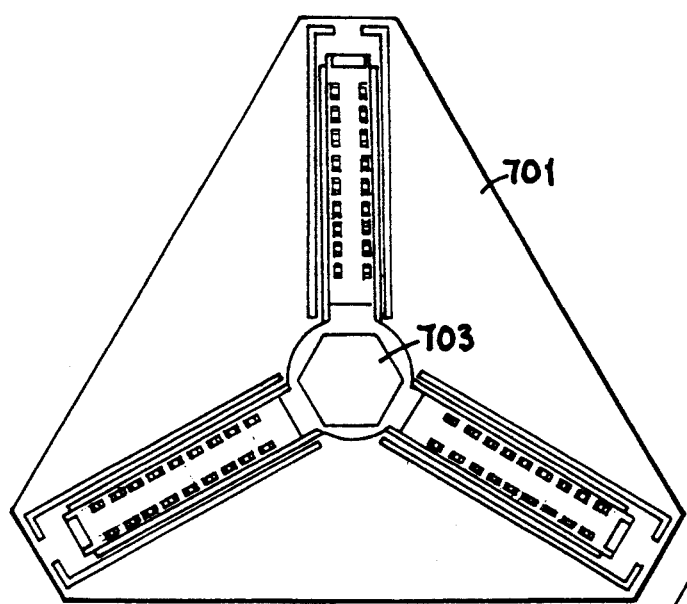
FIG. 7a is a top view of a bottom piece of a test device assembly having a common reception cavity.
Figure 7C:
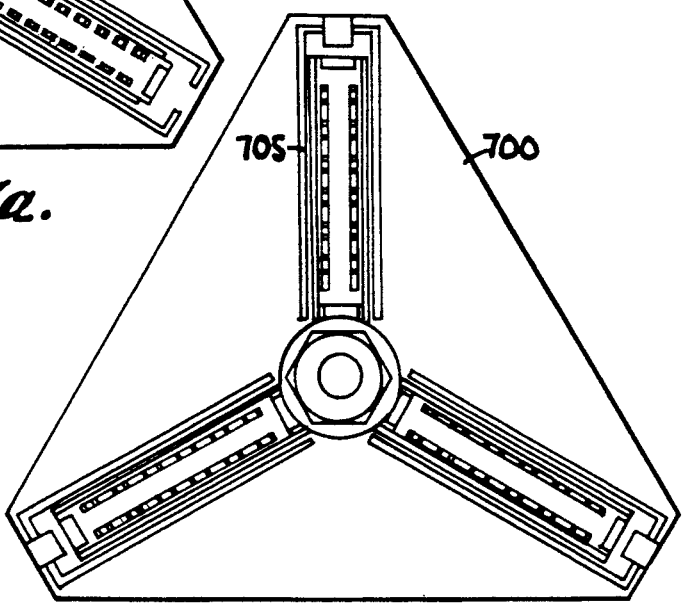
FIG. 7c is a top view of a test device assembly having the bottom piece of FIG. 7a and the top piece of FIG. 7b.
Figure 7B:
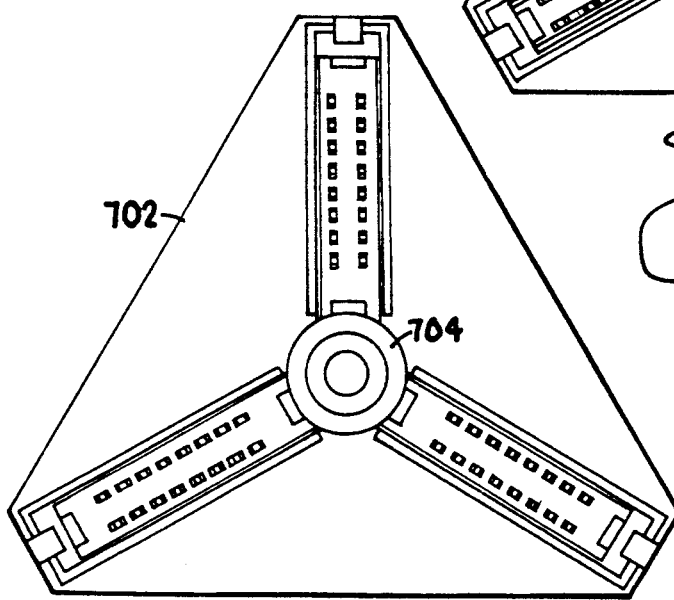
FIG. 7b is a top view of a top piece of a test device assembly having a common reception cavity.

Another embodiment of the multiple test configurations is illustrated in FIGS. 7a-7c. Three test devices 705 are placed in a single holder 700 which has bottom piece 701 and top piece 702. The test devices share a common reception cavity 703. A liquid test sample is introduced into the reception cavity through a central opening 704. Each test strip contains a specific analyte-conjugate probe and the corresponding antibody is coated on latex particles. These strips are placed in the plastic holder in a symmetrical pattern and are individually marked for each specific test. In this design, only a single test sample is applied to the common reception cavity for the multiple analyte testing. The aqueous sample permeates down to the different test strips which allows rehydration of deposited particles. The colored latex particles migrate only through the capillary channel defined by the porous membrane strip. Reference or communicant areas are separated from other analytes with an external reference added. Each chromatographic strip is cut in size to take from 40 microliters to 100 microliters of aqueous sample. The test is usually completed within five to ten minutes. A minus sign or some other symbol placed in each view window area indicates qualitatively the results of the test. Absence of the minus sign, or reference symbol, is an indication that the sample is positive on the particular test.

Figure 8A:
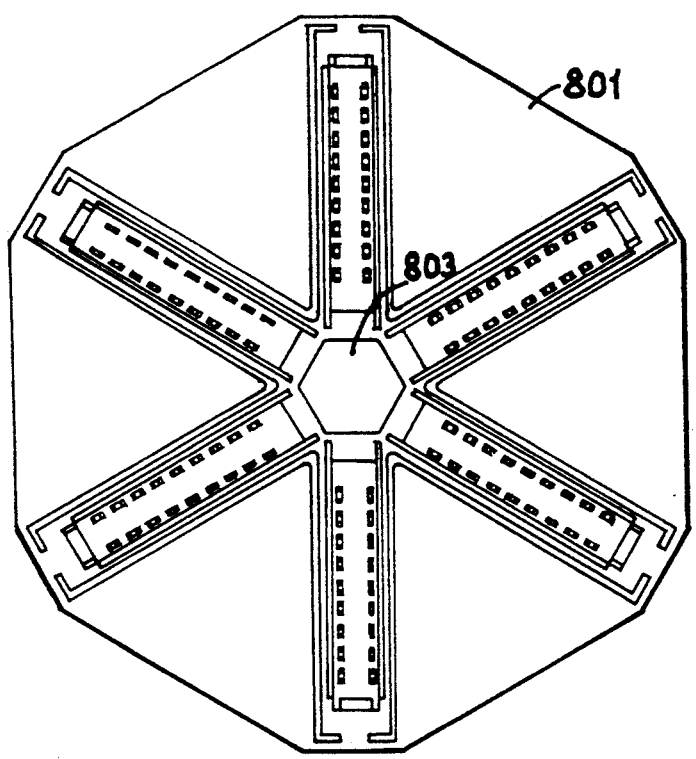
FIG. 8a is a top view of an alternative embodiment of a bottom piece of a test device assembly having a common reception cavity.
Figure 8B:
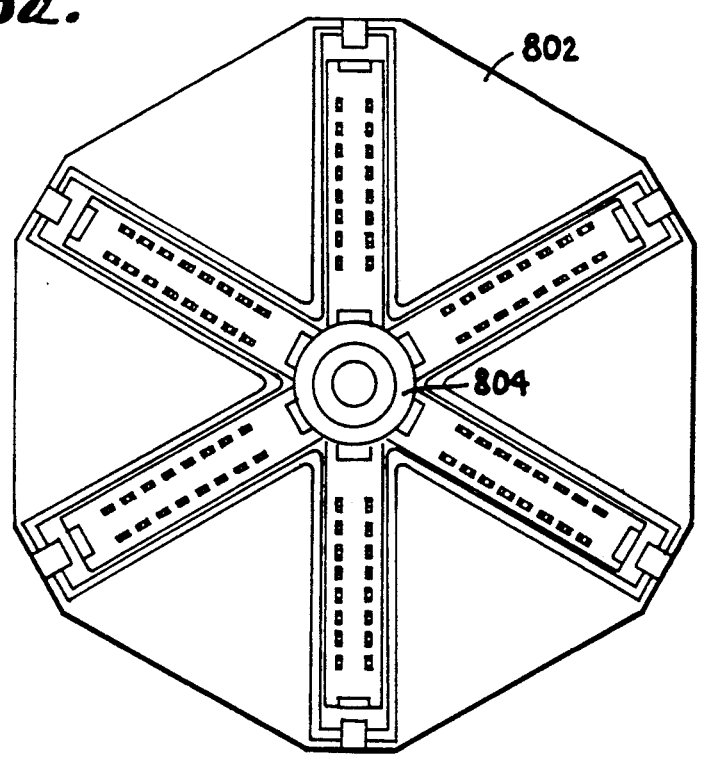
FIG. 8b is a top view of an alternative embodiment of a top piece of a test device assembly having a common reception cavity.
Figure 8C:
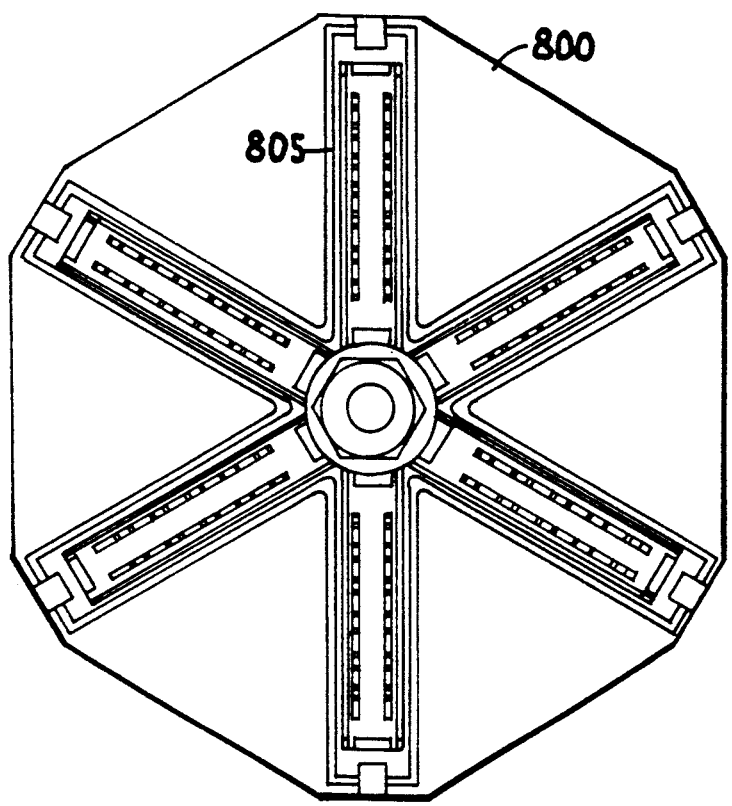
FIG. 8c is a top view of a test device assembly having the bottom piece of FIG. 8a and the top piece of FIG. 8b.

In another multiple test assembly represented by FIGS. 8a-8c, six test devices 805 are assembled in a single holder 800 for the simultaneous testing of, for example, benzoylecgonine, morphine, marijuana, amphetamine, and phencyclidine. The holder has bottom piece 801 and top piece 802. An opening 804 leads to a common reception cavity 803. The test devices and methods are as previously described. A negative result for a single drug or analyte in the multiple test is indicated by the presence of multiple precipitin lines or symbols for the negatives. A test that is positive for an analyte or drug will not show a precipitin end point, and can easily be distinguished from the negative results.

The invention is described primarily with reference to a competition assay wherein any antigens in the sample (representing presence of a drug of abuse or the like) bind to the colored latex particles which have been treated with antibodies responsive to the antigen. The competition upon which this embodiment of the test is based is thus a competition for a limited number of antibody-bearing bonding sites, between latex bodies whose antibodies have been exhausted by presence of the antigen in the sample, and latex bodies whose antibodies have not been blocked by presence of the antigen and remain able to bind to antigen conjugates. It is also possible, and within the scope of the invention, to base the test on a competition between the antigens in the sample and functionally identical antigens or antigen conjugates fixed on the latex particles, for the limited number of binding sites of antibodies fixed on the membrane support. Inasmuch as the mobility of antigens in the body fluid sample is substantially greater than the mobility of antigen conjugates on the latex particles suspended in the body fluid sample, the antigens in the body fluid sample (representing the presence of drugs of abuse or the like) tend to find the binding sites on the membrane support before the latex particles reach the binding sites. As a result, a more direct competition between the relatively more mobile liquid-suspended antigens and the relatively less mobile latex-fixed antigens also provide distinct visually identifiable results depending on the presence or absence of the antigens in the body fluid sample. In the event the antigens are not present, the colored latex particles bearing the antigens eventually flow to and complex with the fixed antibodies at the binding sites, leaving a distinct color mark. In the event antigens are present in the body fluid sample, these antigens are free and relatively mobile, and bind to the fixed antibodies before the less-mobile latex particles arrive at the binding sites. When a latex particle eventually arrives at a given binding site, the binding site has already been exhausted by free antigens in the body fluid sample (which of course are not colored), and no colored mark results.

The following examples are meant to illustrate the invention, and are only representative embodiments of the scope of the invention.

The antigens which can be used in the method of this invention are related to the antigen/antibody conplexation reaction for each of the individual immunological assays. Antigens for the cocaine assay are exemplified by Formula I:

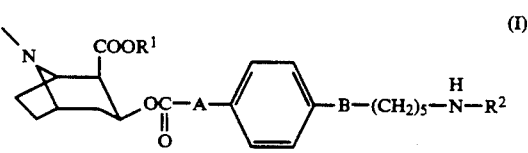

(I)

Where
A = single bond, —CH=CH—, or $CH_2$;
B = NHCO, OCO, or —CH=CH;
$R^1$ = H, $CH_3$, —$CH_2CH_3$, $NHCH_2COOH$;
$R^2$ = —CO— $R^3$, —$CO(CH_2)_2COR^3$;
$R^3$ = serum albumin (bovine, human); hemocyanin, ovalbumin, synthetic polypeptides, serum globulins.

The antigens for the amphetamine/methamphetamine assay are exemplified by Formula II:

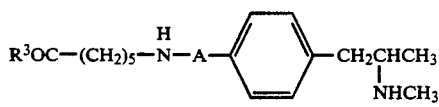

A = single bond, —COCH$_2$O—, —CO(CH$_2$)$_n$ —(CH=CH)$_m$—
R$^3$ = same as defined in formula (I);
n = 0 to 3;
m = 0 or 1.

The antigens for the morphine/opiate assay for conjugates of derivatives reported in Science (1972), 176, 1143-1144, for example.

The antigens for the tetrahydrocannabinoids are conjugates of derivatives reported in FEBS Letters (1975), 55, 257-260, for example.

The antigens for the phencyclidine assay are conjugates of derivatives reported in Res. Comm. Chem. Pathol. Pharmacol. (1979), 25, 547-557, for example.

EXAMPLE 1

Blue Colored latex particles (Bangs Laboratories, Inc., with diameter of from 0.075 microns, stock code P000750PR, up to a diameter of 0.899 microns, #P0008990 CB) are washed with a mixed bed of ion exchange resins (Bio-Rad AG 501-X8, 20-50 mesh). A benzoylecgonine derivative was then covalently bound to the carboxylated latex by the method described (R. S. Molday, et al., J. Cell. Biol. (1975), 64 75-88). The antigen-coated latex beads were suspended in a carrier buffer containing glycerol (0.5%) and polyethylene glycol 6000 (2% wt/vol). This latex suspension was then applied to a porous membrane support (Schleicher & Schuell, Inc. #30270 and #65790; for 8 and 12 micron pore size nitrocellulose membrane, respectively) that was already coated with an antibody specific for benzoylecgonine, at a concentration of from 0.5 or 4 milligrams per milliliter. On another site or section of the membrane, a second, different antibody was absorbed, that is an IgG molecule used to mark the latex particles, and which was applied at a concentration of from 0.2 to 8 milligrams per milliliter.

The volumes of each of the antibody solutions absorbed onto the membrane range from 0.1 to 10 microliters per centimeter. The membranes were then sliced into strips that are from 0.5 to centimeter wide to about 5 centimeters long which are then assembled in housing device 200, for example. To run an assay with this device and configuration, four or five drops of urine are added to the sample well. When the pull tab is removed, the urine will travel down the membrane, to, first, mobilize and suspend the latex particles, which then flow over the two protein probe or communicant lines. If benzoylecgonine is not present in the urine sample, the probe containing the benzoylecgonine specific antibody will complex with the benzoylecgonine conjugate on the colored latex beads to produce a visual precipitin end point. As the latex continues to move down the membrane, the second marker protein will give a precipitin complex to demonstrate the viability of the entire test system. If benzoylecgonine is present in the urine sample, the free benzoylecgonine, a metabolite of cocaine, will compete for the antibody binding sites to prevent the benzoylecgonine bound to the latex from complexation at the antibody probe site on the membrane. Thus, for a sample that contain benzoylecgonine, the latex beads will pass over the antibody probe line and no colored precipitin or complex end point is observed. A negative test result shows up with two color precipitin end point lines. A positive test result shows only one line, for example, corresponding to the reference or control probe or communicant interaction.

EXAMPLE 2

A nylon membrane (Autobloc, Amicon) with a pore size of 5 to 10 microns was used as the solid phase support. A carboxymethyl morphine derivative (B. H. Wainer, et al., Science (1972), 176, 1143-1144), was conjugated to bovine serum albumin, and this protein-hapten conjugate at a molar ratio of 1:10 to 1:20 was absorbed onto the membrane at a concentration of between 0.2 and 10 milligrams per milliliter. The probe line was formed with about 0.1 to 10 microliters per centimeter of this conjugate solution being applied in a 1 millimeter width line. Anti bovine serum albumin antibody at an IgG concentration of 0.1 to 8 milligrams per milliliter was used to form a reference communicant line, for example, and was added at a rate of from 0.1 to 10 microliters per centimeter on the 0.5 to 1 centimeter membrane. Colored latex particles are treated with an aqueous solution of antibody specific for morphine and were then applied to a sucrose foundation on the membrane at a site 2 to 3 centimeters away from the probe lines. After the loaded nylon membranes were completely dried, they were placed into device 408 with two absorbent pads on each end of the membrane, and the complete test device was sealed in a moisture barrier bag with a desiccant such as, for example, silica gel or molecular sieves. To assay for opiates, 4 or 5 drops of test urine sample are introduced into the reception cavity. After about 10 minutes, the latex spheres have completely traversed the membrane. The sample is read as positive or negative for opiates as described in Example 1.

EXAMPLE 3

Polyclonal antibody to amphetamines/methamphetamines were absorbed onto colored latex particles in the concentrations described in Examples 1 and 2, and then deposited and dried in the sample well in device holder (300). The membrane was prepared by the addition of methamphetamine probe line made with a methamphetamine conjugate (L. T. Cheng, et al., FEBS Letters (1973), 36, 339-342) and the reference antibody as described in Example 2. The test for amphetamines/methamphetamine is performed by adding 5 drops of the urine test sample to the reception cavity containing the latex carriers. The suspended latex in the test urine is allowed to stand at ambient temperature for 5 minutes with or without occasional mixing or stirring. The suspension is then transferred to the membrane in device 200 which is contained in holder 300. The end point is read as illustrated in Example 1. A thorough preincubation with urine that is positive for amphetamine/methamphetamine will preclude or prevent the antibody absorbed on the latex from binding to the amphetamines/methamphetamine probe line. The reference line or control is not subject to analyte/antibody complexation because the reference antibody and antigen are not present in the specimen to offer a competition.

EXAMPLE 4

The procedure of Example 3 is followed except that the colored latex particles are dried in the reception cavities of devices 408 or 608 and are kept dry in sealed bags. As in Example 3, the assembly in these devices includes a porous membrane of nitrocellulose, or nylon and an absorbent pad. Latex particles to which antibody to phencyclidine are absorbed and dried in the device 408 and 608 which also contained the membrane charged with phencyclidine conjugate (L. S. Rosenberg and H. V. Vunakis, Res. Comm. in Chem. Phathology and Pharmacology (1979), 25, 547–557). The devices are equilibrated to ambient temperature before a test run if the devices had been refrigerated. About 5 drops of test urine are added to the reception cavity, the latex is brought into suspension by stirring and the incubation of latex with urine and/or analyte-containing urine is allowed to incubate for 5 to 10 minutes. Then the urine sample suspensions are introduced to the capillary channel with a dropper for migration to the membrane enclosed in devices 408 or 608 which are prepared by procedures described in Examples 1 and 2. If necessary, additional drops of urine are added to maintain a flow through the membrane to the pad. The precipitin end points for samples negative or positive for phencyclidine are observed as described in Example 1.

EXAMPLE 5

The procedure for the determination of marijuana metabolites in the urine is similar as described in Example 3 except that a tetrahydrocannabinoid conjugate (M. Cais., et al., FEBS Letters (1975) 55 257–260) is attached to the 10 micron pore size nylon membrane in the presence of a bifunctional linking agent such as, for example, glutataldehyde 0.01% to 0.1%. The appropriate antibodies selected for this test, have an ELISA titre of over 1/4000 with an affinity constant greater than $1 \times 10^9 M^{-1}$. Polyclonal antibody was first purified to the gamma globuline fraction with a DEAE ion exchange column, then dialysed against 50 mM phosphate buffer saline PH 7.4. The dialysate was then diluted in the same buffer to from 0.1 to 10 milligrams per milliliter. The antibody solution at these concentration ranges is employed to coat latex particles through a passive absorption procedure (C. F. Nathan and Z. A. Cohn, J. Exp. Med. (1981) 154, 1539–53). The latex is post blocked with two volumes of normal rabbit serum. Monoclonal antibody against 11-nor-delta-9-tetrahydrocannabinoid-9-carboxylic acid is produced by immunizing animals with an immunogen conjugate tetrahydrocannabinoid keyhole limpet hemocyanin molecule. This antibody is purified through a protein-A affinity column, (Pierce Chemical Co. #21008). The immunoglobulin fraction is added at a concentration of from 0.1 to 10 milligrams per milliliter. The optimum concentration for latex coating is determined by the actual test sensitivity and visibility of the precipitin end point. Devices 408 and 608 are used to determine cannabinoid and metabolites in the urine as described in Example 4.

EXAMPLE 6

A test for benzoylecgonine, the metabolite of cocaine, was configured in device 408 using from 5 to 12 micron pore size nitrocellulose membrane, and following the procedure described in Example 2. The colored latex particles were coated with antibody to benzoylecgonine through a double coating procedure. That is, anti-mouse IgG is coated first on the particles, then the mouse anti-benzoylecgonine is absorbed. A benzoylecgonine conjugate was absorbed on the membrane as the communicant or probe for the end point as the preceeding examples, a reference probe was added to the porous support. The assay was run exactly as described in Example 2.

Other assays for opiates, amphetamines/methamphetamines, cannabinoids and phencylidine, for example, can be configured using the same formulations but using appropriate antibodies, antigens and antigen conjugates for each desired analyte test.

EXAMPLE 7

A dual test for benzoylecgonine and morphine on one porous membrane was accomplished in device 408 by using the procedure described in Example 2 except that nitrocellulose (8 microns) was used in place of the nylon porous support. Colored latex particles were individually coated with antibody for each analyte, and the coated latex particles were then mixed. The latex particles were of the same color, but different colored particles could be used for each analyte, or, alternatively, the colored latex particles were treated sequentially with each antibody according to specific antibody titres and absorptivity. Appropriate and distinct probe lines, prepared from a specific analyte-containing molecule conjugated to either bovine serum albumin, keyhole limpet hemocyanin or a polypeptide for each analyte, were applied to the membrane at different sites as described in Examples 1 and 2. The test was performed exactly as described in Example 1, and each probe or communicant area was read for a specific analyte test. With this configuration, benzoylecgonine was detected at the 300 to 400 nanogram per milliliter level, and morphine was detected below 300 nanograms per milliliter in urine.

EXAMPLE 8

Preparation of Benzoylecgonine—BSA Conjugate

A mixture of 4.0 g (15.1 mmole) of 6-(Carbobenzyloxyamino) caproic acid, 4.07 g (31 mmole) of 1-hydroxybenzotriazole hydrate, and 35 mL of 1,2-dimethoxyethane was treated all at once with 3.11 g (15.1 mmole) of 1,3-dicyclohexylcarbodiimide. The mixture was stirred for one hour as the urea precipitated. Then, N-ethylmorpholine was added to adjust the pH to 7.1–7.2. 4-Aminobenzoic acid (2.18 g, 15.1 mmole) was added, and the suspension was stirred at ambient temperature for 18 hours. The reaction was poured into iced dilute hydrochloric acid solution (300 mL), the precipitate was filtered and the aqueous layer was extracted with ethyl acetate (5×50 mL). The combined organic extracts were washed with brine, dried ($Na_2SO_4$) and the solution was concentrated to about 50 mL and chilled. The isolated solid was recrystallized from methanol giving 1.93 g (33%) of a 4-(6-carbobenzyloxyaminocaproyl) aminobenzoic acid, m.p. 179°–181° C.

A solution of 1.93 g (4.5 mmole) of the above compound in 20 mL of dry tetrahydrofuran and 5 mL of 1,2-dimethoxyethane was treated with 0.52 g (2.5 mmole) of 1,3-dicyclohexylcarbodiimide. This mixture was stirred and heated at 45° C. for 72 hours. Then, triethylamine (0.6 mL), 4-dimethylaminopyridine (250 mg) and ecgonine hydrochloride (0.55 g, 2.4 mmole) were added, and the reaction was concentrated in vacuo to a dark, semi-solid residue which was taken up in a minimum of dichloromethane and applied atop a column packed with 60.0 g of Merck "60" silica gel. The column was eluted with a gradient of 20 to 40% of methanol in ethyl acetate. The homogeneous fractions showed an Rf on silica gel plates of 0.16 in 3:1 methanol-/acetate containing 1% of NH4OH solution. There was obtained 230 mg of [4-(6-carbobenzyloxy-aminocaproyl) aminobenzoyl] ecgonine as an amorphous powder.

This ecgonine derivative (70 mg) was dissolved in 2.5 mL of 32% hydrobromic acid dissolved in acetic acid. The resulting solution was stirred at 5° C. for one hour, and then allowed to warm to room temperature. After being stirred an additional 3 hours, ether (50 mL) was added and the supernatant was decanated from the white precipitate. This process of washing with ether was repeated three times. The white solid was dried in vacuo, and the hygroscopic hydrobromide salt was dissolved in 6 mL of 5% of dimethyformamide in water, and the pH was adjusted to 7.0–7.1 with 5% aqueous tetramethylammonium hydroxide. Then, 50 mg of N-hydroxysuccinimide was dissolved in 4 ml of a 25% solution of 1,2-dimethoxylethane in water and this was added to the reaction mixture. The mixture was then cooled to 5° C. and 70 mg of bovine serum albumin was added followed by 70 mg of 1-ethyl-3-(3-dimethylaminopropyl) carbodiimide hydrochloride. After one hour, an additional 15 mg of the diimide was added and stirring was continued at from 5° to 15° C. for 18 hours. This mixture was then dialyzed against 0.1M NaCl (2×4 liters) for 48 hours to give the conjugate solution which was used as is for the probe line for the benzoylecgonine/cocaine assay.

EXAMPLE 9

Preparation of Cinnamoylecgonine—BSA Conjugate

The procedure of Example 8 was followed except that 4-aminocinnamic acid was substituted for 4-aminobenzoic acid to afford 4-(6-carbobenzyloxyaminocaproyl) aminocinnamic acid, mp 142°–144° C. The preparation of the cinnamoylecgonine-BSA conjugate was exactly as described in Example 8 for the benzoylecgonine-BSA conjugate by substituting the above cinnamoyl derivative for the benzoyl derivative.

EXAMPLE 10

Preparation of a Phenylacetylecgonine-BSA Conjugate

The procedure for Example 8 was followed except that 4-aminophenylacetic acid was substituted for 4-aminobenzoic acid to afford 4-(6-carbobenzyloxyaminocaproyl) aminophenylacetic acid, mp 136°–138° C. The preparation of the phenylacetyl-BSA conjugate was exactly as described in Example 8 for the benzoylecgonine-BSA conjugate by substituting the above phenylacetyl derivative for the benzoyl derivative.

EXAMPLE 11

Preparation of an Amphetamine/Methamphetamine-BSA Conjugate

In a dry round bottom flask was placed 1.0 g (6.05 mmole) of 4-hydroxymethamphetamine, 1.62 g (1.05 mL, 7.26 mmole) of N-methylbis (trifluoroacetamide) and 2 mL of sieve-dried dimethylformamide. This mixture was stirred and heated at 65° C. for 2.5 hours, and then the mixture was stirred at room temperature for 18 hours. The reaction was diluted with iced brine, the product was extracted repeatedly with ethyl acetate and the water-washed organic extracts were dried over Na2SO4, concentrated and azeotroped with toluene to afford about 1.5 g of yellow, oily N-trifluoroacetamido-4-hydroxymethamphetamine.

The above trifluoroacetamide (1.5 g) was dissolved in 5 mL of anhydrous 1,2-dimethoxyethane, the solution was cooled to 5° C. and sodium hydride (60% in mineral oil) (0.344 g, 8.6 mmole) was added. After stirring the cool suspension for one-half hour at room temperature, t-butyl bromoacetate (1.68 g, 8.6 mmole) in 2 mL of DME was added portionwise, and the reaction mixture was stirred at room temperature for 18 hours. The reaction was poured into ice water, extracted with ethyl acetate, and the washed, dried and concentrated solution gave 2.3 g of 4-(t-butylcarboxy) methoxy-N-trifluoracetamidomethamphetamine as a liquid which showed an Rf of 0.83 on silica gel with 3:1 hexane/ethyl acetate.

The above t-butyl ester (2.32 g, 4.94 mmole) was dissolved in 3 mL of dichloromethane, and 0.5 mL of 1,3-dimethoxybenzene was added. The solution was cooled in ice and trifluoroacetic acid (5 mL), which was previously cooled, was added. The reaction was then stirred at room temperature for 2 days. The solvents were evaporated at room temperature at 10 mm of pressure, and the dark residue was taken up in ether and the product was then extracted into 10% solution sodium carbonate (4×15 mL). The aqueous extracts were acidified with dilute HCl to pH 2, and the product was extracted into ethyl acetate. The water-washed, dried and concentrated solution gave 1.92 g of crude, oily 4-carboxymethoxy-N-trifluoroacetamidomethamphetamine.

The above free acid (1.92 g, 4.81 mmole) was dissolved in 4 mL of 1,2-dimethoxyethane and 2 mL of tetrahydrofuran and 0.61 g (5.29 mmole) of N-hydroxysuccimimide and 1.09 g (5.29 mmole) of 1,3-dicyclohexylcarbodiimide were added. This mixture was stirred at room temperature overnight, N-ethylmorpholine (2.5 mL) and methyl 6-aminocaproate (1.05 g, 7.23 mmole) were added. Stirring was continued for an additional 24 hours, and the reaction was diluted with brine and the product extracted into dichloromethane. The organic extracts were washed with cold 1N HCl, brine and water and the dried concentrated product was chromatographed over 45 g of silica gel in a gradient of 50% to 80% of ethyl acetate in hexanes to provide 300 mg of the light pinkish, oily 4-[(carbomethoxypentyl) carboxamido] methoxy-N-trifluoroacetamidomethamphetamine, with an Rf on silica thin layer plates of 0.58 with 2:1 ethyl acetate/hexanes.

This methyl ester (300 mg, 0.58 mmole) was dissolved in 8 mL of methanol and a solution of 3.63 g of potassium hydroxide in 4 mL of water was added. After being stirred at room temperature for 2 days, the methanol was evaporated, 5 mL of water was added and the pH was adjusted to 6.8–7.0 with dilute HCl to give a volume of about 30 mL. Then, 1,2-dimethoxylethane (20 mL) was added followed by 134 mg (1.164 mmole) of N-hydroxsuccinimide. The mixture was cooled to 10° C. and 43 mg of BSA were added followed by 126 mg (0.918 mmole) of 1-ethyl-3-(3-dimethylaminopropyl) carbodimide hydrochloride which was added in portions over 30 minutes. The reaction was stirred at 10° C. for 4 hours and an additional 50 mg of EDCI was added. After 7 hours of stirring at 10° C., the reaction was then stirred at room temperature for 2 hours, and glycine (250 mg) was added to quench the reaction. This mixture was then dialyzed against 0.1M NaCl at room temperature for 48 hours (2×4 liters) to give the amphetamine/methamphetamine conjugate solution used in the assay.

We claim:

1. An analytical test device for producing a visually-perceptible indication of whether particular non-protein antigens are present via competition assay for particular non-protein antigens representing drugs of abuse, consisting essentially of:

a test kit housing having means for introduction of a body fluid sample at a first end of said housing and means defining a flow path for the body fluid sample to a second end of said housing;

a supply of microscopic colored latex particles disposed adjacent to the means for introduction of the body fluid sample along the flow path, the colored latex particles becoming suspended in the body fluid sample and moving with flow of the body fluid sample along the flow path from said first end toward said second end, the latex particles being sensitized with a supply of antibodies for the non-protein antigen at least on a surface thereof, said antibodies being responsive to said non-protein antigens and being operable to complex therewith;

a chromatographic membrane support disposed within the test kit housing and being impregnated at a first predetermined site along the flow path downstream of the colored latex particles towards said second end with an immobilized drug conjugate probe sensitive to said antibodies on the latex particles, and operable to complex therewith; and, means for exposing the colored latex particles at said first end to the body fluid sample for substantially complete reaction of the non-protein antigens in the body fluid sample with the antibodies for the non-protein antigen on the latex particles, prior to the body fluid sample reaching the first predetermined site along the flow path;

whereby when said non-protein antigens are not present in the body fluid sample the latex particles accumulate at the first predetermined site by complexing of the antibodies on the latex particles with the drug conjugate probe on the membrane support to leave a visually perceptible colored mark of a same color as the colored latex particles, and when said non-protein antigens are present in the body fluid sample, complexing of the non-protein antigens to the supply of antibodies on the latex particles substantially exhausts the antibody supply on the latex particles such that the latex particles cannot complex to the immobilized drug conjugate probe, leaving no visually perceptible mark at the predetermined site.

2. The analytical test device according to claim 1, wherein the latex particles further comprise a supply of second immunoreaction protein antibodies bonded to the latex particles, the second immunoreaction antibodies being non-responsive to the non-protein antibodies and being responsive to protein antigens, the chromatographic membrane support being impregnated at a second predetermined site along the flow path downstream of the first predetermined site further towards the second and with a further immobilized immunoreaction antibody probe sensitive to said second immunoreaction protein and operable to complex therewith, the second and further immunologic probe complexing the latex particles to the membrane support at said second predetermined site leaving a visually perceptible colored mark of a same color as the colored latex particles at said second predetermined site, thereby indicating at least one of completion of the test and operability of the test device.

3. The analytical test device according to claim 1, wherein the test kit housing defines a reception cavity adjacent said means for introduction of the body fluid sample at the first end and said latex particles are immobilized at the reception cavity prior to introduction of the body fluid sample.

4. The analytical test device according to claim 3, wherein the test kit housing includes means for initiating flow along the flow path from the reception cavity to the membrane support.

5. The analytical test device according to claim 4, wherein said means for initiating flow includes two sections of said housing, said sections disposed for relative movement with respect to each other, the flow path being closed when the two sections are abutted and opened when the two sections are relatively displaced.

6. The analytical test device according to claim 3, further comprising a first absorptive pad in communicating relationship with the means for introduction of the body fluid sample at said first end.

7. The analytical test device according to claim 6, further comprising at least one additional absorptive pad toward said second end and downstream of the first absorptive pad and the membrane support, the additional absorptive pad receiving flow of the body fluid sample following passage thereof through and along the membrane support.

8. The analytical test device according to claim 1, wherein said immobilized drug probe contains an antigen conjugate for one of a drug of abuse or a metabolite of a drug of abuse.

9. The analytical test device according to claim 8, wherein the membrane support is a porous material and the body fluid sample proceeds along the flow path of the membrane support by capillary action.

10. The analytical test device according to claim 8, wherein the drugs of abuse are at least one of cocaine, cannabinoids, amphetamine/methamphetamine, phencyclidene, and opiates.

11. The analytical test device according to claim 8, wherein the colored latex particles are finally blocked with protein to substantially completely coat the colored latex particles.

12. The analytical test device according to claim 8, wherein the housing defines at least one capillary passage along the flow path dimensioned to draw the body fluid by surface tension.

13. The analytical test device according to claim 12, wherein the membrane support is a porous material and the flow path proceeds along the membrane support by capillary action of the porous material.

14. The analytical test device according to claim 8, wherein the colored latex particles are substantially formed as latex spheres.

15. The analytical test device according to claim 14, wherein the latex spheres have a diameter of about 0.1 micron to 1.0 micron.

16. An analytical test assembly for producing a visually-perceptible indication of whether particular non-protein antigens are present via simultaneous multiple competition assays for said particular non-protein antigens representing drugs of abuse, consisting essentially of:

a plurality of test kit housings each having means for introduction of a body fluid sample at a first end of said housings and means defining a flow path for the body fluid sample to a second end within said housings;

a supply of microscopic colored latex particles disposed adjacent to each of the means for introduction of the body fluid sample along the flow path, the colored latex particles becoming suspended in the body fluid sample and moving with flow of the body fluid sample along the flow path from said first end toward said second end, the colored latex particles being sensitized with a supply of antibodies for the non-protein antigen at least on a surface thereof, said antibodies being responsive to said non-protein antigens and being operable to complex therewith;

a chromatographic membrane support disposed within each of the test kit housings and being impregnated at a first predetermined site along the flow path downstream of the colored latex particles towards said second end with an immobilized drug conjugate probe sensitive to said antibodies on the latex particles, and operable to complex therewith;

means for exposing the colored latex particles at said first end to the body fluid sample for substantially complete reaction of the non-protein antigens in the body fluid sample with the antibodies for the non-protein antigen on the colored latex particles, prior to the body fluid sample reaching the predetermined site along the flow path whereby when said non-protein antigens are not present in the body fluid sample the colored latex particles accumulate at the predetermined site downstream of said first end by complexing of the antibodies on the colored latex particles with the drug conjugate probe on the membrane support to leave a visually perceptible colored mark of a same color as the colored latex particles, and when said non-protein antigens are present in the body fluid sample, complexing of the non-protein antigens to the supply of antibodies on the colored latex particles substantially exhausts the antibody supply on the colored latex particles such that the colored latex particles cannot complex to the immobilized drug conjugate probe, leaving no visually perceptible mark at the predetermined site; and, a holder for maintaining a plurality of analytical test devices, each said analytical test device including one of said test kit housings, said supply of microscopic colored latex particles and chromatographic membranes in fixed relationship, comprising:

a holder body adapted to removably receive the plurality of analytical test devices, and means for securing the plurality of analytical test devices in the holder.

17. The analytical test assembly according to claim 16, wherein the securing means is a press fit.

18. The analytical test assembly according to claim 16, wherein the plurality of analytical test devices are disposed parallel to each other.

19. The analytical test assembly according to claim 16, wherein the holder defines at least one external well dimensioned to receive the body fluid sample.

20. The analytical test assembly according to claim 16, wherein the holder defines a plurality of external wells each dimensioned to receive a portion of the body fluid sample, and each corresponding to one of the plurality of analytical test devices in the holder.

21. The analytical test assembly according to claim 16, wherein the holder defines a common reception cavity having means for communicating a portion of the body fluid sample introduced therein to each of the plurality of analytical test devices.

22. The analytical test assembly according to claim 21, wherein the plurality of analytical test devices are each disposed radially outwardly from the common reception cavity.

23. An analytical test device for competition assay for particular non-protein antigens representing drugs of abuse, consisting essentially of:

a test kit housing having means for introduction of a body fluid sample at a first end of said housing and means defining a flow path for the body fluid sample to a second end within said housing;

a supply of microscopic colored latex particles disposed adjacent to the means for introduction of the body fluid sample along the flow path, the colored latex particles becoming suspended in the body fluid sample and moving with flow of the body fluid sample along the flow path from said first end toward said second end, the colored latex particles being sensitized at least on a surface thereof with at least one of said antigens representing drugs of abuse and a functionally identical antigen conjugate;

a chromatographic membrane support disposed within the test kit housing and being impregnated at a first predetermined site along the flow path with an immobilized antibody responsive to said antigen and said antigen conjugate, and operable to complex therewith; and means in proximity with said means for introduction of the body fluid, for allowing the colored latex particles and the body fluid sample to mix and for allowing the mixed colored latex particles and the body fluid sample to flow along the flow path from said first end toward said second end to the predetermined site such that the body fluid sample reaches the predetermined site prior to the colored latex particles, whereby presence of the antigen in the body fluid is indicated by lack of a colored mark at the predetermined site, due to exhaustion of said antibodies by binding with the antigen in the body fluid sample, and absence of the antigen in the body fluid sample is indicated by presence of the colored mark at the predetermined site due to binding of the latex particles to the antibodies the colored mark being of a same color as the colored latex particles.

24. The analytical test device according to claim 23, wherein said means for allowing the colored latex particles and the body fluid to mix and to flow toward the predetermined site includes a porous membrane between the means for introduction of the body fluid and the predetermined site, said body fluid sample traversing the porous membrane more quickly than the colored latex particles.

* * * * *